United States Patent [19]
Belliotti et al.

[11] Patent Number: 6,087,364
[45] Date of Patent: Jul. 11, 2000

[54] DOPAMINE D4 RECEPTOR ANTAGONISTS

[75] Inventors: Thomas Richard Belliotti, Saline; David Juergen Wustrow, Ann Arbor, both of Mich.

[73] Assignee: Warner-Lambert Company, Morris Plains, N.J.

[21] Appl. No.: 09/015,576

[22] Filed: Jan. 29, 1998

Related U.S. Application Data

[60] Provisional application No. 60/037,060, Feb. 12, 1997.

[51] Int. Cl.$^7$ ........................ A61K 31/496; C07D 417/14
[52] U.S. Cl. ............................... 514/254.02; 514/253.01; 514/254.08; 514/323; 544/364; 544/367; 544/373; 546/200
[58] Field of Search .................................. 544/364, 373, 544/367; 514/253

[56] References Cited

U.S. PATENT DOCUMENTS

| | | | |
|---|---|---|---|
| 4,355,031 | 10/1982 | Demerson et al. | 424/250 |
| 4,999,355 | 3/1991 | Comte et al. | 514/253 |
| 5,681,954 | 10/1997 | Yamamoto et al. | 544/114 |

FOREIGN PATENT DOCUMENTS

| | | |
|---|---|---|
| 7-33744 | 2/1995 | Japan . |
| WO 93/16073 | 2/1993 | WIPO . |

OTHER PUBLICATIONS

Belliotti et al., "Isoindolinone Enantiomers Having Affinity for the Dopamine D4 Receptor," Bioorg. & Med. Chem. Let., vol. 8, No. 12, pp. 1499–1502, 1998.

*Primary Examiner*—Emily Bernhardt
*Attorney, Agent, or Firm*—Charles W. Ashbrook

[57] ABSTRACT

Compounds that are antagonists of dopamine D4 receptors, methods of treating psychosis and schizophrenia using the compounds, and pharmaceutically acceptable compositions that contain the dopamine D4 receptor antagonists are disclosed.

3 Claims, No Drawings

DOPAMINE D4 RECEPTOR ANTAGONISTS

This application claims the benefit of U.S. Provisional Application No. 60/037,060 filed Feb. 12, 1997.

FIELD OF THE INVENTION

This invention relates to compounds that are antagonists at dopamine D4 receptors, to methods of treating psychosis and schizophrenia using a compound that is an antagonist at dopamine D4 receptors, and to pharmaceutically acceptable compositions that contain a dopamine D4 receptor antagonist.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are referred to as dopamine receptor antagonists. It is also well-known that dopamine receptor antagonists are useful in the treatment of schizophrenia and psychosis.

Recently, it has been discovered that more than one type of dopamine receptor exists and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. D2 subtype receptors are located in both the limbic region of the brain, which is associated with cognition and emotional function, and in the striatum, which is associated with motor effects. D4 receptors are found in higher concentrations in the frontal cortex and limbic regions, which are associated with cognitive and emotional function.

Antipsychotic drugs that are D2 subtype receptor antagonists have been used to treat psychosis and schizophrenia, but have undesirable extrapyramidal side effects and produce tardive dyskinesia. In contrast, D4 receptor antagonists show a lack of extrapyramidal side effects and tardive dyskinesia. Moreover, it has been observed that the levels of dopamine D4 receptors are elevated in schizophrenics.

Thus, it would be useful to develop compounds that are selective D4 antagonists for the treatment of psychosis and schizophrenia.

SUMMARY OF THE INVENTION

The present invention provides a compound of the Formula I

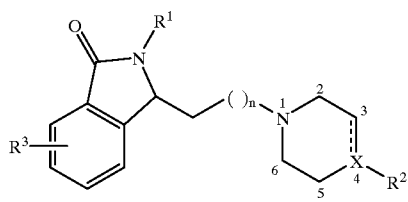

I wherein
X is CH, C, or N where when X is CH or N, a single bond exists between X and the adjacent carbon atom at position 3 and when X is C, a double bond exists between X and the adjacent carbon atom at position 3;

$R^1$ is hydrogen or $C_1$–$C_6$ alkyl;

$R^2$ is phenyl or phenyl substituted with at least one of halogen, $C_1$–$C_6$ alkyl, $C_1$–$C_6$ alkoxy, $C_1$–$C_6$ thioalkoxy, or 2-pyridinyl substituted with $C_1$–$C_6$ alkyl;

$R^3$ is hydrogen, halogen, $C_1$–$C_6$ alkyl, $C_1$–$C_6$ alkoxy, or $C_1$–$C_6$ thioalkoxy; and n is 1, 2, or 3.

In a preferred embodiment of Formula I, X is N.
In a preferred embodiment of Formula I, X is C.
In a preferred embodiment of Formula I, X is CH.
In a preferred embodiment of Formula I, n is 1.
In a preferred embodiment of Formula I, n is 2.
In a preferred embodiment of Formula I, n is 3.

In a preferred embodiment of Formula I, X is N, $R^1$ is hydrogen, $R^2$ is phenyl or phenyl substituted with at least one of halogen, $C_1$–$C_6$ alkyl, $C_1$–$C_6$ alkoxy, $C_1$–$C_6$ thioalkoxy, or 2-pyridinyl substituted with $C_1$–$C_6$ alkyl; $R^3$ is hydrogen, halogen, $C_1$–$C_6$ alkyl, $C_1$–$C_6$ alkoxy, or $C_1$–$C_6$ thioalkoxy; and n is 1.

In a more preferred embodiment of Formula I, X is N, $R^1$ and $R^3$ are hydrogen, $R^2$ is phenyl or phenyl substituted with at least one of halogen, $C_1$–$C_6$ alkyl, $C_1$–$C_6$ alkoxy, $C_1$–$C_6$ thioalkoxy, or 2-pyridinyl substituted with $C_1$–$C_6$ alkyl; $R^3$ is hydrogen, halogen, $C_1$–$C_6$ alkyl, $C_1$–$C_6$ alkoxy, or $C_1$–$C_6$ thioalkoxy; and n is 1.

In a most preferred embodiment of Formula I, the compounds are:

3-{2-[4-(3,4-Dimethyl-phenyl)-piperazin-1-yl]-ethyl}-2,3-dihydro-isoindol-1-one;

3-[2-(4-P-Tolyl-piperazin-1-yl)-ethyl]-2,3-dihydro-isoindol-1-one;

3-[2-(4-Phenyl-piperazin-1-yl)-ethyl]-2,3-dihydro-isoindol-1-one;

3-[2-(4-p-Chlorophenyl-piperazin-1-yl)-ethyl]-2,3-dihydro-isoindol-1-one;

3-[2-(4-p-Methoxyphenyl-piperazin-1-yl)-ethyl]-2,3-dihydro-isoindol-1-one;

3-[2-(4-Naphthalen-2-yl-piperazin-1-yl)-ethyl]-2,3-dihydro-isoindol-1-one;

3-[2-(4-(4,5-Dimethyl-thiazol-2-yl)-piperazin-1-yl)-ethyl]-2,3-dihydro-isoindol-1-one; or 3-[2-(4-(Diphenylmethylene)-piperidin-1-yl)-ethyl]-2,3-dihydro-isoindol-1-one.

Also, in a most preferred embodiment of Formula I, the compounds are a (+) or (−) enantiomer.

Also provided by the present invention is a method of treating psychosis, the method comprising administering to a patient suffering therefrom a therapeutically effective amount of a compound of Formula I.

Also provided by the present invention is a method of treating schizophrenia, the method comprising administering to a patient suffering therefrom a therapeutically effective amount of a compound of Formula I.

Also provided by the present invention is a pharmaceutically acceptable composition that comprises a compound of Formula I.

DETAILED DESCRIPTION OF THE INVENTION

The present invention provides a compound of the Formula I

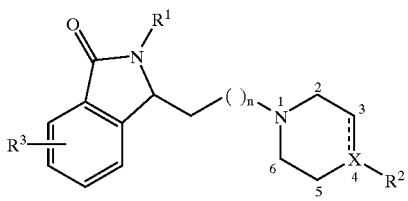

I

X is CH, C, or N where when X is CH or N, a single bond exists between X and the adjacent carbon atom at position 3 and when X is C, a double bond exists between X and the adjacent carbon atom at position 3;

$R^1$ is hydrogen or $C_1$–$C_6$ alkyl;

$R^2$ is phenyl or phenyl substituted with at least one of halogen, $C_1$–$C_6$ alkyl, $C_1$–$C_6$ alkoxy, $C_1$–$C_6$ thioalkoxy, or 2-pyridinyl substituted with $C_1$–$C_6$ alkyl;

$R^3$ is hydrogen, halogen, $C_1$–$C_6$ alkyl, $C_1$–$C_6$ alkoxy, or $C_1$–$C_6$ thioalkoxy; and n is 1, 2, or 3.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxyl" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The symbol "–" means a bond.

The atoms in the indoline group are numbered as shown below:

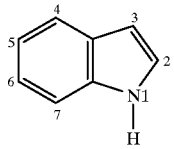

The term "patient" includes humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ration, and effective for their intended use, as well as the zwitterionic forms, where possible, of the compounds of the invention.

The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts, and the like. These may include cations based on the alkali and the alkaline earth metals such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine ethylamine, and the like. (See, for example, Berge S. M., et al., "Pharmaceutical Salts," *J. Pharm. Sci.,* 66:1–19 (1977) which is incorporated herein by reference.)

Examples of pharmaceutical acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

The term "prodrug" refers to compounds that are rapidly transformed in vivo to yield the parent compound of the above formulas, for example, by hydrolysis in blood. A thorough discussion is provided in Higuchi T. and Stella V., "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one customary inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservative, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is sufficient. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

The compounds provided by this invention are prepared utilizing readily available starting materials and employing common synthetic methodologies well-known to those skilled in the art. In a typical synthesis, an isoindole substituted at the 1-position with an alkyl group bearing a leaving group on the terminal carbon is reacted with a suitably substituted cyclic amine to effect displacement of the leaving group, thereby producing an invention compound. This general scheme is depicted below:

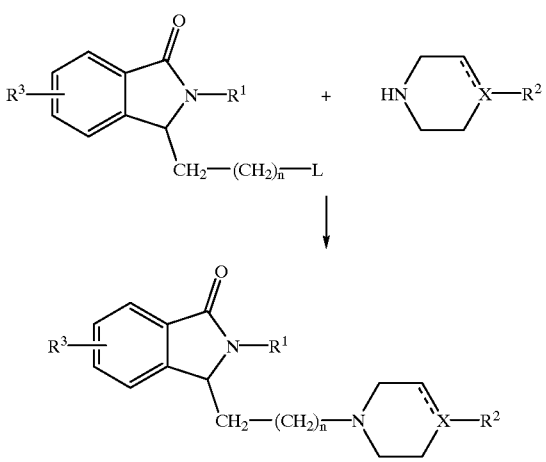

wherein L is a leaving group such as bromo, iodo, paratoluenesulfonyloxy or trimethylsilyloxy. The displacement reaction generally is carried out in an organic solvent dichloromethane or acetonitrile, and normally is complete within about 2 to about 24 hours when conducted at about 20° C. to about 60° C. The product is readily isolated and purified by normal procedures, for example crystallization, chromatography, and the like. Synthesis of starting materials and final products is illustrated more fully in Chart I.

The synthesis of invention compounds is further illustrated by the following detailed examples.

solid is stirred into 300 mL of $CH_2Cl_2$ for 1 hour. The solid is removed by filtration, and the filtrate is evaporated to give 12 g (56% yield) of 2,3-dihydro-3-oxo-1H-isoindole-1-acetic acid methyl ester.

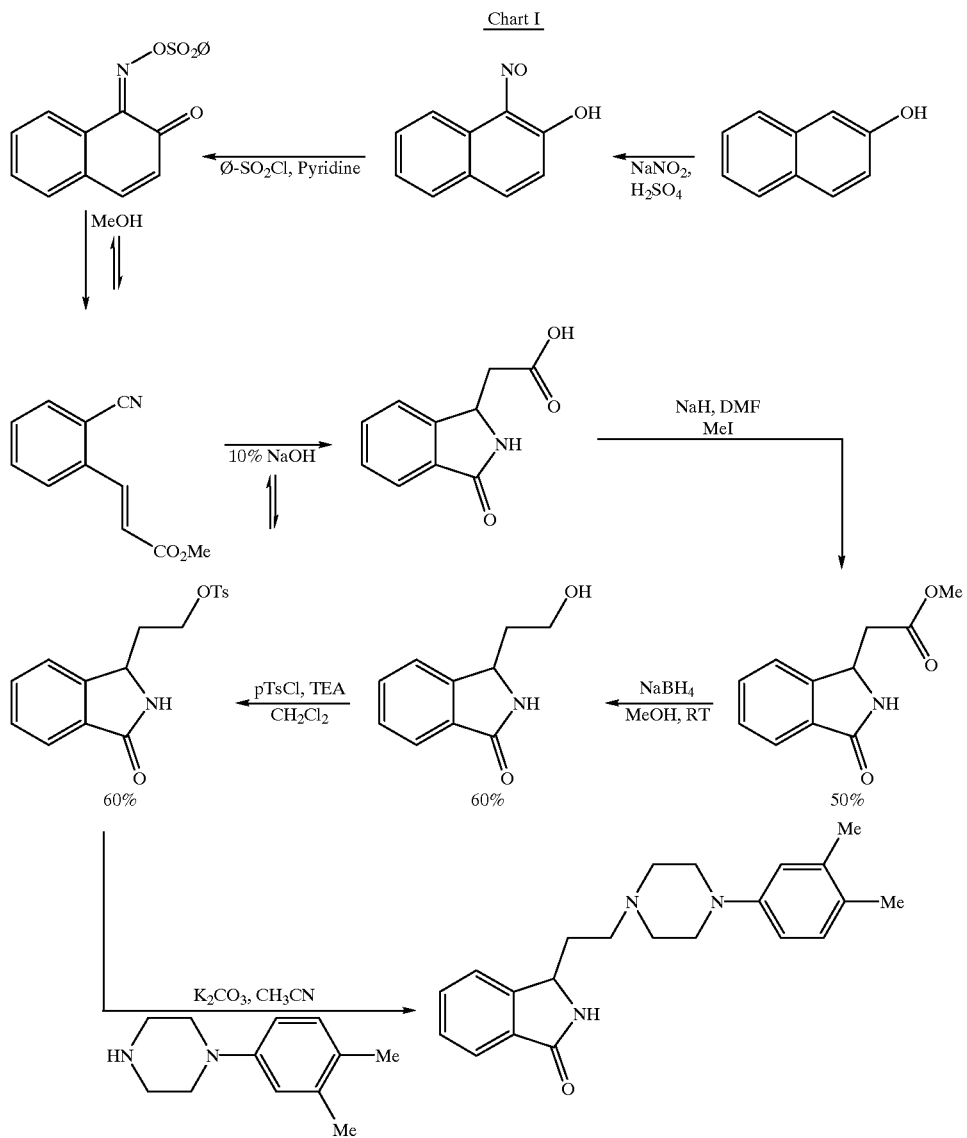

Chart I

EXAMPLE 1

Preparation of 2,3-Dihydro-3-oxo-1H-isoindole-1-acetic acid methyl ester

A solution of 2,3-dihydro-3-oxo-1H-isoindole-1-acetic acid (Rowe F. M., et al., *J. Chem. Soc.*, 1098, 1936) (20 g, 104.6 mmol) in 100 mL of DMF is added to a suspension of NaH (2.5 g, 104.6 mmol) in 200 mL of DMF at room temperature under argon. Some cooling is required during the addition to keep the mixture at room temperature. The mixture is stirred at room temperature for 30 minutes. Methyl iodide (14.8 g, 104.6 mmol) is added, and the mixture is stirred at room temperature overnight. The reaction is quenched by addition of 5 mL of acetic acid, and the DMF is evaporated. Residual DMF is removed by heating the wet solid in a steam bath under high vacuum. The dried NMR (300 MHz, $CDCl_3$): δ 3.1 1H(dd), 3.8 3H(s), 4.9 1H(dd), 6.9 1H(s), 7.4 1H(d), 7.5 1H(m), 7.6 1H(m), 7.9 1H(d).

EXAMPLE 2

Preparation of 1,3-Dihydro-3-(2-hydroxyethyl)-2H-isoindol-1-one 2,3-Dihydro-3-oxo-1H-isoindole-1-acetic acid methyl ester (1.5 g, 7.5 mmol) is added to a solution of $NaBH_4$ (1.4 g, 37.6 mmol) in 50 mL of methanol at room temperature, and the mixture is stirred overnight. The reaction is quenched by addition of gaseous HCl until the pH=1. The methanol is evaporated, and the remaining solid is stirred in 100 mL of $CH_2Cl_2$ for 15 minutes. The solid is removed by filtration through Celite® 545. Evaporation of the filtrate gives 1.3 g (90% yield) of 1,3-dihydro-3-(2-hydroxyethyl)-2H-isoindol-1-one as an oil.

NMR (300 MHz, $CDCl_3$): δ 1.8 1H(s), 2.4 1H(s), 4.0 2H(s), 5.0 1H(d), 7.5 2H(m), 7.7 1H(m), 7.9, 1H(d).

EXAMPLE 3

Preparation of 1,3-Dihydro-3-(2-tosylethyl)-2H-isoindol-1-one

Tosyl chloride (3.4 g, 17.7 mmol) is added to a solution of TEA (5.1 g, 50.8 mmol) and 1,3-dihydro-3-(2-hydroxyethyl)-2H-isoindol-1-one (3.0 g, 16.9 mmol) in 50 mL of $CH_2Cl_2$ at room temperature under argon. After 12 hours, the reaction mixture is extracted with $H_2O$ (2×100 mL) and dried over $Na_2SO_4$. Evaporation of the solvent gives 4.2 g (75% yield) of 1,3-dihydro-3-(2-tosylethyl)-2H-isoindol-1-one; mp=146–149° C. (dec) after recrystallization from ethyl acetate.

EXAMPLE 4

Preparation of 3-{2-[4-(3,4-Dimethyl-phenyl)-piperazin-1-yl]-ethyl}-2,3-dihydro-isoindol-1-one A solution of 1,3-dihydro-3-(2-tosylethyl)-2H-isoindol-1-one (4.2 g, 12.7 mmol), 1-(3,4-dimethylphenyl)-piperazine (2.6 g, 13.9 mmol), and $K_2CO_3$ (8.8 g, 63.3 mmol) in 150 mL of $CH_3CN$ is warmed to reflux overnight under argon. After being cooled to room temperature, the solvent is evaporated, and the remaining solid is stirred in 100 mL of $H_2O$ for 20 minutes. The solid is collected, dried, and recrystallized from $CH_3CN$ to give 2.7 g (60% yield) of 3-{2-[4-(3,4-dimethyl-phenyl)-piperazin-1-yl]-ethyl}-2,3-dihydro-isoindol-1-one; mp=167–169° C.

EXAMPLE 5

Preparation of (−)-3-{2-[4-(3,4-Dimethyl-phenyl)-piperazin-1-yl]-ethyl}-2,3-dihydro-isoindol-1-one and (+)-3-{2-[4-(3,4-Dimethyl-phenyl)-piperazin-1-yl]-ethyl}-2,3-dihydro-isoindol-1-one 3-{2-[4-(3,4-Dimethyl-phenyl)-piperazin-1-yl]-ethyl}-2,3-dihydro-isoindol-1-one (2.77 g, 7.9 mmol) and d-malic acid (1.1 g, 7.9 mmol) are dissolved in 800 mL of hot $CH_3CN$. The solution is concentrated to 200 mL and allowed to cool to room temperature overnight. The precipitate is collected, recrystallized from 200 mL of $CH_3CN$ and converted to the free base by extraction from 1.0 N NaOH with $CH_2Cl_2$. Drying over $Na_2SO_4$ and evaporation of the solvent gives 0.09 g of (−)-3-{2-[4-(3,4-dimethyl-phenyl)-piperazin-1-yl]-ethyl}-2,3-dihydro-isoindol-1-one.

Analysis Calculated: C, 75.61, H, 7.79, N, 12.02. Found: C, 75.40, H, 7.83, N, 11.88. Rotation=−30.7 (5.0 mg/mL in MeOH).

The mother liquors are combined and evaporated. The salt remaining is converted to the free base by extraction from 1.0 N NaOH with $CH_2Cl_2$. The organic layer is dried over $Na_2SO_4$ and evaporated to give 2.0 mmol of the free base. It is dissolved in 100 mL of hot isopropanol with 1-malic acid (0.27 g, 2.0 mmol). The solution is concentrated to 40 mL and cooled to room temperature overnight. The precipitate is collected and converted to its free base by extraction from 1.0 N NaOH with $CH_2Cl_2$. Drying over $Na_2SO_4$ and evaporation of solvent gives 0.33 g of (+)-3-{2-[4-(3,4-Dimethyl-phenyl)-piperazin-1-yl]-ethyl}-2,3-dihydro-isoindol-1-one.

Analysis: Found C, 75.33, H, 7.76, N, 11.88. Rotation=+32.5 (6.5 mg/mL in MeOH).

EXAMPLE 6

Preparation of 1,3-Dihydro-2-methyl-3-(2-hydroxyethyl)-2H-isoindol-1-one

Sodium borohydride (4.1 g, 109.4 mmol) is added to a solution of 2,3-dihydro-2-methyl-3-oxo-1H-isoindole-1-acetic acid methyl ester (*Synthesis*, 1986:755) (4.8 g, 21.9 mmol) in 50 mL of MeOH at room temperature and stirred overnight. The reaction is quenched by addition of 100 mL of 2.0 N NaOH, and the MeOH is evaporated. The solution is extracted with $CH_2Cl_2$ (3×100 mL). The extracts are combined and dried over $Na_2SO_4$ and evaporated to give 2.2 g (52% yield) of 1,3-dihydro-2-methyl-3-(2-hydroxyethyl)-2H-isoindol-1-one.

NMR ($CDCl_3$, 400 MHz): δ 1.6 1H(s), 2.1 1H(m), 2.3 1H(m), 3.1 3H(s), 3.5 2H(m), 4.6 1H(t), 7.5 2H(m), 7.6 1H(m), 7.8 1H(m).

EXAMPLE 7

Preparation of 1,3-Dihydro-2-methyl-3-(2-tosylethyl)-2H-isoindol-1-one p-Toluene sulfonyl chloride (2.3 g, 12.1 mmol) is added to a solution of TEA (3.5 g, 34.5 mmol) and 1,3-dihydro-2-methyl-3-(2-hydroxyethyl)-2H-isoindol-1-one (2.2 g, 11.5 mmol) in 50 mL of $CH_2Cl_2$ at room temperature under argon. The mixture is stirred at room temperature overnight and washed with water (3×50 mL). The organic layer is dried over $Na_2SO_4$ and evaporated to give an oil which is chromatographed in ethyl acetate over silica gel to give 1.5 g (38% yield) of 1,3-dihydro-2-methyl-3-(2-tosylethyl)-2H-isoindol-1-one.

NMR ($CDCl_3$, 400 MHz): δ 2.2 1H(m), 2.4 4H(m), 3.0 1H(s), 3.8 2H(t), 4.4 1H(m), 7.3 3H(m), 7.4 2H(m), 7.6 2H(d), 7.7 1H(d).

The following compounds were prepared according to the procedure of Example 4.

| Example | Compound | Melting Point ° C. |
|---|---|---|
| 8 | 3-[2-(4-P-Tolyl-piperazin-1-yl)-ethyl]-2,3-dihydro-isoindol-1-one | 178–181 |
| 9 | 3-[2-(4-Phenyl-piperazin-1-yl)-ethyl]-2,3-dihydro-isoindol-1-one | 183–185 |
| 10 | 3-[2-(4-p-Chlorophenyl-piperazin-1-yl)-ethyl]-2,3-dihydro-isoindol-1-one | 205–207 |
| 11 | 3-[2-(4-p-Methoxyphenyl-piperazin-1-yl)-ethyl]-2,3-dihydro-isoindol-1-one | 174–176 |
| 12 | 3-[2-(4-Naphthalen-2-yl-piperazin-1-yl)-ethyl]-2,3-dihydro-isoindol-1-one | 245–248 |
| 13 | 3-[2-(4-(4,5-Dimethyl-thiazol-2-yl)-piperazin-1-yl)-ethyl]-2,3-dihydro-isoindol-1-one | 174–176 |
| 14 | 3-[2-(4-(Diphenyhlmethylene)-piperidin-1-yl)-ethyl]-2,3-dihydro-isoindol-1-one | 146–148 |
| 15 | 3-{2-[4-(5-Methyl-pyridin-2-yl)-piperazin-1-yl]-ethyl}-2,3-dihydro-isoindol-1-one | 147–149 |
| 16 | 3-{2-[4-(3,4-Dimethyl-phenyl)-piperazin-1-yl]-ethyl}-2,3-dihydro-2-methyl-isoindol-1-one | 105–107 |
| 17 | 3-[2-(4-p-Chlorophenyl-piperazin-1-yl)-ethyl]-2,3-dihydro-2- | 97–99 |

-continued

| Example | Compound | Melting Point ° C. |
|---------|----------|--------------------|
| | methyl-isoindol-1-one | |
| 18 | 3-[2-(4-p-Methoxyphenyl-piperazin-1-yl)-ethyl]-2,3-dihydro-2-methyl-isoindol-1-one | 112–115 |

The compounds of this invention have been evaluated in standard biological assays which confirm their dopamine D4 receptor antagonist activity. Typical assays are described below:

Cell Lines Expressing Dopamine Receptor Isoforms

A cell line expressing human dopamine D2 (Long form) receptors was purchased from Oregon Health Sciences University, Portland, Oreg. The D2 receptor cDNA was subcloned into an expression vector, pRc/CMV. The plasmids were transfected by electroporation into CHO K1 cells. A single stable transfectant, resistant to the antibiotic G418, was isolated and selected for use in the binding studies. For D4 binding, CHO K1 cells stably transfected to express the human recombinant dopamine D4.2 receptor subtype, as described by Shih, et al., "The Expression and Functional Characterization of Human Dopamine D4.2 Receptor in CHO K1 Cells," Soc. Neurosci., 21(Part 1): 621 (1995).

Cell Culture and Preparation of Cell Membranes

CHO K1 cells expressing either human D2 and D4.2 receptors were grown in 162 cm$^2$ culture flasks in F12 medium (Gibco Laboratories, Grand Island, N.Y.) supplemented with 10% fetal bovine serum (FBS, Hyclone, Logan, Utah) in an atmosphere of 5% $CO_2$/95% air at 37° C. Cells were grown until confluent, after which growth medium was removed and replaced with 0.02% ethylene diamine tetracetate (EDTA) in a phosphate-buffered saline solution (Sigma Chemical Co., St. Louis, Mo.) and scraped from the flasks. The cells were centrifuged at about 1000× g for 10 minutes at 40° C. and then resuspended in TEM buffer (25 mM Tris-HCl, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20,000× g at 40° C. for 20 minutes. Then the pellets were resuspended in appropriate buffer at 1 mL/flask and stored at −70° C. until used in the receptor binding assay.

Receptor Binding Assays: D2, D4.2 Dopamine Receptors

A cell membrane preparation (400 μμL) was incubated in triplicate with 50 μL [$^3$H]spiperone (0.2 nM for D2, 0.2 nM for D4.2), 50 μL buffer, or competing drugs where appropriate to give a final volume of 0.5 mL. After 60 minutes incubation at 25° C., the incubations were terminated by rapid filtration through Whatmann GF/B glass fibre filters (soaked for 1 hour in 0.5% polyethylenimine) on a cell harvester, with three washes of 1 mL ice-cold buffer. Individual filter disks containing the bound ligand were placed in counting vials with 4 mL of scintillation fluid (Ready Gel, Beckman Instrument Inc., Fullerton, Calif.) and then counted in a Beckman LS-6800 liquid scintillation counter at an efficiency of 45%. Nonspecific binding was defined in presence of 1 mM of haloperidol.

Blockade of Amphetamine-Stimulated Locomotion (BASL) in Rats

Justification

Hyperactivity of brain dopamine (DA) neuronal systems is believed to contribute to the symptomology of schizophrenia. This hypothesis is supported, in part, by the ability of drugs such as the indirect DA agonist, amphetamine, to exacerbate schizophrenia. The stimulatory effect of amphetamine can be blocked by one of two mechanisms: a postsynaptic blockade of DA receptors, or by the action of DA autoreceptor agonists at inhibitory presynaptic DA receptor sites. Currently available antipsychotic drugs are DA receptor antagonists; however, these compounds can also cause extrapyramidal side effects apparently due to complete postsynaptic receptor blockade. Antipsychotic agents produce sedation (manifested as decreased locomotion) in normal animals, as well as in animals treated with psychomotor stimulants by reducing the access of endogenous DA to postsynaptic receptors in the brain.

Methods

Male Sprague-Dawley rats (Harlan Labs) were used for these studies. Drugs were dissolved in saline or water and administered either orally (PO) or intraperitoneally (IP) in volumes of 5 mL/kg. Saline control rats and amphetamine (0.5 mg/kg IP) control rats are included with each study (n=4–6 rats per treatment group). for the IP studies, amphetamine is given 20 minutes prior to the drug, after which a 30 minute locomotor activity test is conducted. For the oral study, drug is dosed 30 minutes prior to test, while amphetamine is given 15 minutes prior to test, which allows time for oral absorption. Locomotor activity (centimeters travelled per 30 minute test) is measured in 16"×16" open chambers. Amphetamine generally produces a 2- to 3-fold increase in locomotion over saline controls. Drug effects are reported as percent reversal of amphetamine-stimulated locomotion. Significant changes in amphetamine-stimulated locomotion, relative to amphetamine-treated controls, were determined by t-test. The dose which would reverse amphetamine-stimulated locomotion by 50% ($ED_{50}$) and the 95% confidence limits were estimated by regression analysis.

Data Calculation

Saturation and competition binding data were analyzed using an iterative nonlinear least-square curve-fitting Ligand program. In competition experiments, apparent $K_i$ values were calculated from $IC_{50}$ values by method of Cheng and Prusoff, "Relationship Between the Inhibition Constant ($K_i$) and the Concentration of Inhibitor Which Causes 50% Inhibition ($IC_{50}$) of an Enzymatic Reaction," Biochem. Pharmacol., 22:3099–3108 (1973). Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_d$ values were measured for the interaction of various ligands with the receptor. These were: [$^3$H]spiperone binding, human D2, 0.116+0.1 and human D4.2, 0.093+0.005 nM (n=3). The test results are presented in Table 1.

TABLE 1

Biological Data Data

| Compound Name | D4 Binding ($K_i$, nM) | D2 Binding ($K_i$, nM) | BASL $ED_{50}$, mg/kg PO |
|---------------|------------------------|------------------------|--------------------------|
| 3-[2-(4-P-Tolyl-piperazin-1-yl)-ethyl]-2,3-dihydro-isoindol-1-one | 12.4 | >5882 | <1 |
| 3-[2-(4-Phenyl-piperazin-1-yl)-ethyl]-2,3-dihydro- | 24.5 | — | — |

TABLE 1-continued

Biological Data Data

| Compound Name | D4 Binding ($K_i$, nM) | D2 Binding ($K_i$, nM) | BASL $ED_{50}$, mg/kg PO |
|---|---|---|---|
| isoindol-1-one | | | |
| 3-[2-(4-p-Chlorophenyl-piperazin-1-yl)-ethyl]-2,3-dihydro-isoindol-1-one | 27.8 | >5882 | — |
| 3-[2-(4-p-Methoxyphenyl-piperazin-1-yl)-ethyl]-2,3-dihydro-2-methyl-isoindol-1-one | 37.3 | >5882 | — |
| 3-[2-([4-(4,5-Dimethyl-thiazol-2-yl)-piperazin-1-yl)-ethyl]-2,3-dihydro-isoindol-1-one | 20.8 | >5882 | — |
| 3-[2-(4-(Diphenyl-methylene)-piperidin-1-yl)-ethyl]-2,3-dihydro-isoindol-1-one | 99.7 | 2147 | — |
| 3-{2-[4-(3,4-Dimethyl-phenyl)-piperazin-1-yl]-ethyl}-2,3-dihydro-isoindol-1-one | 8.77 | 1842 | 3 |
| (−)-3-{2-[4-(3,4-Dimethyl-phenyl)-piperazin-1-yl]-ethyl}-2,3-dihydro-isoindol-1-one | 7.8 | >5882 | 1.5 |
| (+)-3-{2-[4-(3,4-Dimethyl-phenyl)-piperazin-1-yl]-ethyl}-2,3-dihydro-isoindol-1-one | 42 | 2748 | — |
| 3-{2-[4-(5-Methyl-pyridin-2-yl)-piperazin-1-yl]-ethyl}-2,3-dihydro-isoindol-1-one | 22.6 | >5882 | — |
| 3-{2-[4-(3,4-Dimethyl-phenyl)-piperidin-1-yl]-ethyl}-2,3-dihydro-isoindol-1-one | 9.27 | 1209 | — |

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, reference numerals are merely for convenience and are not to be in any way limiting, and the invention may be practiced otherwise than as specifically described.

REFERENCES CITED

Berge S. M., et al., "Pharmaceutical Salts," *J. Pharm. Sci.,* 66:1–19 (1977).

*Biochem. Pharmacol.,* 22:3099–3108 (1973).

Higuchi T. and Stella V., "Pro-drugs as Novel Delivery Systems," Vol. 14 of the A.C.S. Symposium Series, and in *Bioversible Carriers in Drug Design*, ed. Edward B. Roche, American Pharmaceutical Association and Pergamon Press, 1987.

Shih, et al., "The Expression and Functional Characterization of Human Dopamine D4.2 Receptor in CHO K1 Cells," *Soc. Neurosci.,* 21(Part 1):621 (1995).

What is claimed is:

1. A compound that is 3-[2-(4-(4,5-Dimethyl-thiazol-2-yl)-piperazin-1-yl)-ethyl] -2,3 -dihydro-isoindol-1-one.

2. A method of treating psychosis, the method comprising administering to a patient suffering therefrom a therapeutically effective amount of a compound of claim 1.

3. A method of treating schizophrenia, the method comprising administering to a patient suffering therefrom a therapeutically effective amount of a compound of claim 1.

* * * * *